US011439528B2

(12) United States Patent
Gilbert, Jr.

(10) Patent No.: US 11,439,528 B2
(45) Date of Patent: Sep. 13, 2022

(54) LEG RESTRAINT SYSTEM AND METHODS OF USE THEREOF

(71) Applicant: Henry L. Gilbert, Jr., Five Points, AL (US)

(72) Inventor: Henry L. Gilbert, Jr., Five Points, AL (US)

(*) Notice: Subject to any disclaimer, the term of this patent is extended or adjusted under 35 U.S.C. 154(b) by 420 days.

(21) Appl. No.: 16/586,191

(22) Filed: Sep. 27, 2019

(65) Prior Publication Data

US 2020/0100930 A1 Apr. 2, 2020

Related U.S. Application Data

(60) Provisional application No. 62/737,980, filed on Sep. 28, 2018.

(51) Int. Cl.
*A61F 5/37* (2006.01)
*A41F 9/00* (2006.01)

(52) U.S. Cl.
CPC .............. *A61F 5/37* (2013.01); *A41F 9/002* (2013.01)

(58) Field of Classification Search
CPC .............. A61F 5/37; A61F 5/3715; A61F 5/3761–3776; A61F 5/3792; A41F 9/00–025; A45F 2200/00; B65D 63/00; B65D 63/10; B65D 63/1018–1027; B65D 63/109; B65D 63/18; A47D 13/08; A47D 13/086; A05B 75/00; A05B 75/005; A47C 7/50; A47C 7/506; A47C 7/5062; A47C 7/52

See application file for complete search history.

(56) References Cited

U.S. PATENT DOCUMENTS

| | | | | |
|---|---|---|---|---|
| 480,523 A | * | 8/1892 | Smith | A41F 9/002 2/312 |
| 1,642,105 A | * | 9/1927 | Eastin | A41F 9/002 24/323 |
| 2,295,806 A | * | 9/1942 | Peterson | A61F 5/3715 128/878 |
| 3,496,935 A | * | 2/1970 | Bell, Jr. | A61F 5/01 128/882 |
| 4,172,453 A | * | 10/1979 | Leckie | A61F 5/3723 128/878 |
| 4,728,553 A | * | 3/1988 | Daniels | A44B 18/00 297/466 |
| 5,481,764 A | * | 1/1996 | Nelson | A61F 5/37 4/559 |

(Continued)

*Primary Examiner* — Michelle J Lee
(74) *Attorney, Agent, or Firm* — Mathew L. Grell; Grell & Watson Patent Attorneys LLC

(57) ABSTRACT

A leg restraint system to hold a person's thighs together while seated with bent legs, including a strap having a first strap end and a second strap end, a buckle, the buckle having a first latchable end and a second latchable end, wherein the first latchable end is affixed to the first strap end and the second latchable end affixed to the second strap end, one or more keepers configured to gather the first strap end and a second strap end, a bungee binder, the bungee binder configured to hold the strap in a stored position and, thus, functions to be easily used to carry or transport the leg restraint system and utilize the leg restraint system to clasp, cinch, and hold a seated passengers bent legs in parallel and prevent their bent legs from spreading to a V-spread and encroaching on another adjacent traveler's designated leg space.

6 Claims, 6 Drawing Sheets

(56) References Cited

U.S. PATENT DOCUMENTS

| | | | | |
|---|---|---|---|---|
| 5,713,548 A * | 2/1998 | Boyer | ............... | F16M 13/00 |
| | | | | 248/205.2 |
| 5,715,578 A * | 2/1998 | Knudson | ............ | B65D 63/10 |
| | | | | 24/17 AP |
| 6,083,183 A * | 7/2000 | Yang | ................ | A61F 5/028 |
| | | | | 2/311 |
| 6,202,236 B1 * | 3/2001 | Price | .................. | A47C 16/00 |
| | | | | 297/464 |
| 7,832,807 B2 * | 11/2010 | Shickle | ............... | A61G 5/10 |
| | | | | 297/466 |
| 2003/0005557 A1 * | 1/2003 | Renn | ................ | B65D 63/16 |
| | | | | 24/115 G |
| 2012/0004079 A1 * | 1/2012 | Hyacinth | ........ | A63B 69/0059 |
| | | | | 482/92 |
| 2013/0232731 A1 * | 9/2013 | Schradin | ........ | B65D 63/1018 |
| | | | | 24/16 R |
| 2019/0060101 A1 * | 2/2019 | Muthal | ............ | A61F 5/0104 |

* cited by examiner

LEG RESTRAINT SYSTEM AND METHODS OF USE THEREOF

CROSS-REFERENCE TO RELATED APPLICATIONS

To the full extent permitted by law, the present United States Non-provisional Patent Application hereby claims priority to and the full benefit of, U.S. Provisional Application No. 62/737,980, filed on Sep. 28, 2018, entitled "Strap Restraint System and Methods Of Use Thereof", which is incorporated by reference herein in its entirety.

FIELD OF THE DISCLOSURE

The present disclosure is directed to a strap restraint system and methods of use thereof. More specifically, the present disclosure is directed to a strap restraint used to retrain or hold a seated persons legs together at the knee.

BACKGROUND

As populations swell in most countries local officials and politicians pursue ads, warning signs, regulations, and rules for all sorts of human behaviors deemed unacceptable. In New York, Seattle, Netherlands, Japan, and Spain law makers have either issued ad campaigns against behaviors deemed unacceptable or outlawed travelers from pursuing behaviors deemed unacceptable. A new threat posed by some is when a traveler is occupying more than their fair share of leg room while travelling on ever-crowded public transportation. For example, a traveler may not sit in a posture with their bent legs V-spread apart encroaching on another adjacent traveler's designated leg space or prevent use of adjacent seating, called "manspreading". Manspreading is defined as a sitting posture, a sort of V-shaped slouch, effectively occupying two, sometimes three, seats. New ad campaigns and regulations are aimed at curbing rude behavior like manspreading, she-bagging, and wearing large backpacks on crowded public transportation.

One approach to prevent manspreading is to sit with your knees parallel. One disadvantage or drawback to this approach is that, manspreading is habitual and comfortable and relieves any closure or compacting pressure on the testicles.

Therefore, it is readily apparent that there is a need for a leg restraint system that can be easily used to clasp, cinch, and hold a seated passengers bent legs comfortably in parallel and prevent their bent legs from spreading to a V-spread and encroaching on another adjacent traveler's designated leg space or prevent use of adjacent seating, called "manspreading". The instant disclosure is designed to address at least certain aspects of the problems or needs discussed above.

SUMMARY

Briefly described, in an example embodiment, the present disclosure may overcome the above-mentioned disadvantages and may meet the recognized need for a leg restraint system for use with a seated bent leg traveler, configured of a strap having a first strap end and a second strap end, a buckle, the buckle having a first mating end and a second mating end, wherein the first mating end slidably affixed to the first strap end and the second mating end slidably affixed to the second strap end, one or more keepers configured to gather the first strap end and a second strap end therebetween the first strap end and the second strap end, and a bungee binder, the bungee binder having a looped flex cord formed integral to a ball, the bungee binder affixed to the strap, wherein the looped flex cord surrounds the strap in a coiled configuration to hold the coiled strap in a rolled position for transport and, thus, functions to be easily used to carry or transport the leg restraint system and utilize the leg restraint system to clasp, cinch, and hold a seated passengers bent legs in parallel and prevent their bent legs from spreading to a V-spread and encroaching on another adjacent traveler's designated leg space or prevent use of adjacent seating, called "manspreading".

Accordingly, in another aspect, the present disclosure may be utilized to hold a seated passengers bent legs in parallel and prevent their bent legs from spreading to a V-spread and encroaching on another adjacent traveler's designated leg space or prevent use of adjacent seating, called "manspreading".

In an exemplary embodiment a leg restraint system to hold a person's thighs together while seated with bent legs, including a strap having a first strap end and a second strap end, a buckle, the buckle having a first latchable end and a second latchable end, wherein the first latchable end is affixed to the first strap end and the second latchable end affixed to the second strap end, one or more keepers configured to gather the first strap end and a second strap end, a bungee binder, the bungee binder configured to hold the strap in a stored position.

In another exemplary embodiment of a method of holding a user's thighs together while seated with bent legs, including determining whether an adjacent traveler AT is present next to the user, providing a leg restraint system with a strap having a first strap end and a second strap end, a buckle, said buckle having a first latchable end and a second latchable end, wherein said first latchable end is affixed to said first strap end and said second latchable end affixed to said second strap end, one or more keepers configured to gather said first strap end and a second strap end, and a bungee binder having a ball and a stretch cord configured as a loop extending therefrom said ball, said bungee binder configured to hold said strap in a stored position, releasing said stretch cord from around said ball to unravelling said strap, unlatching said buckle to separate said a first latchable end and said second latchable end, wrapping said strap around the thighs of user, latching buckle by inserting said first latchable end into said second latchable end.

A feature of the leg restraint system and methods of use thereof may include to properly align bent legs while seated to better maintain a person's personal space with an inexpensive apparatus to prevent manspreading.

A feature of the leg restraint system and methods of use thereof is to provide a variety of circumference settings and combinations of circumference settings using an adjustable strap and quick release buckle.

A feature of the leg restraint system and methods of use thereof is to better assist the traveler in many ways to include posture and holding or binding things or objects together or to attach objects to other objects, like a pack to another piece of luggage.

A feature of the leg restraint system and methods of use thereof is to provide a removable leg restraint apparatus capable of maintaining personal space or gap between travelers on airplanes, trains, busses, sports and other entertainment seating and other public and private seating arrangements.

A feature of the leg restraint system and methods of use thereof is to enable quick exit from the strap by standing up, pulling your knees together and walking out of the leg restraint system.

A feature of the leg restraint system and methods of use thereof is to provide a non-metallic restraint system with no metal parts for TSA purposes.

A feature of the leg restraint system and methods of use thereof is to provide a washable restraint apparatus.

A feature of the leg restraint system and methods of use thereof is to provide a compact foldable or coilable design to condense the apparatus for travel purposes.

A feature of the leg restraint system and methods of use thereof is to provide an ergonomic design to relieve inner thigh gripping tension during long or extended travel time while still maintain an adequate gap for testicle spacing and cooling.

These and other features of the leg restraint system and methods of use thereof will become more apparent to one skilled in the art from the prior Summary and following Brief Description of the Drawings, Detailed Description of exemplary embodiments thereof, and Claims when read in light of the accompanying Drawings or Figures.

BRIEF DESCRIPTION OF THE DRAWINGS

The present leg restraint system and methods of use thereof will be better understood by reading the Detailed Description of the Preferred and Selected Alternate Embodiments with reference to the accompanying drawing Figures, in which like reference numerals denote similar structure and refer to like elements throughout, and in which.

It is to be noted that the drawings presented are intended solely for the purpose of illustration and that they are, therefore, neither desired nor intended to limit the disclosure to any or all of the exact details of construction shown, except insofar as they may be deemed essential to the claimed disclosure.

DETAILED DESCRIPTION

In describing the exemplary embodiments of the present disclosure, as illustrated in FIGS. 1, 2, 3, 4, 5A, 5B, and 6 specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples, and are merely examples among other possible examples.

Figure 1:
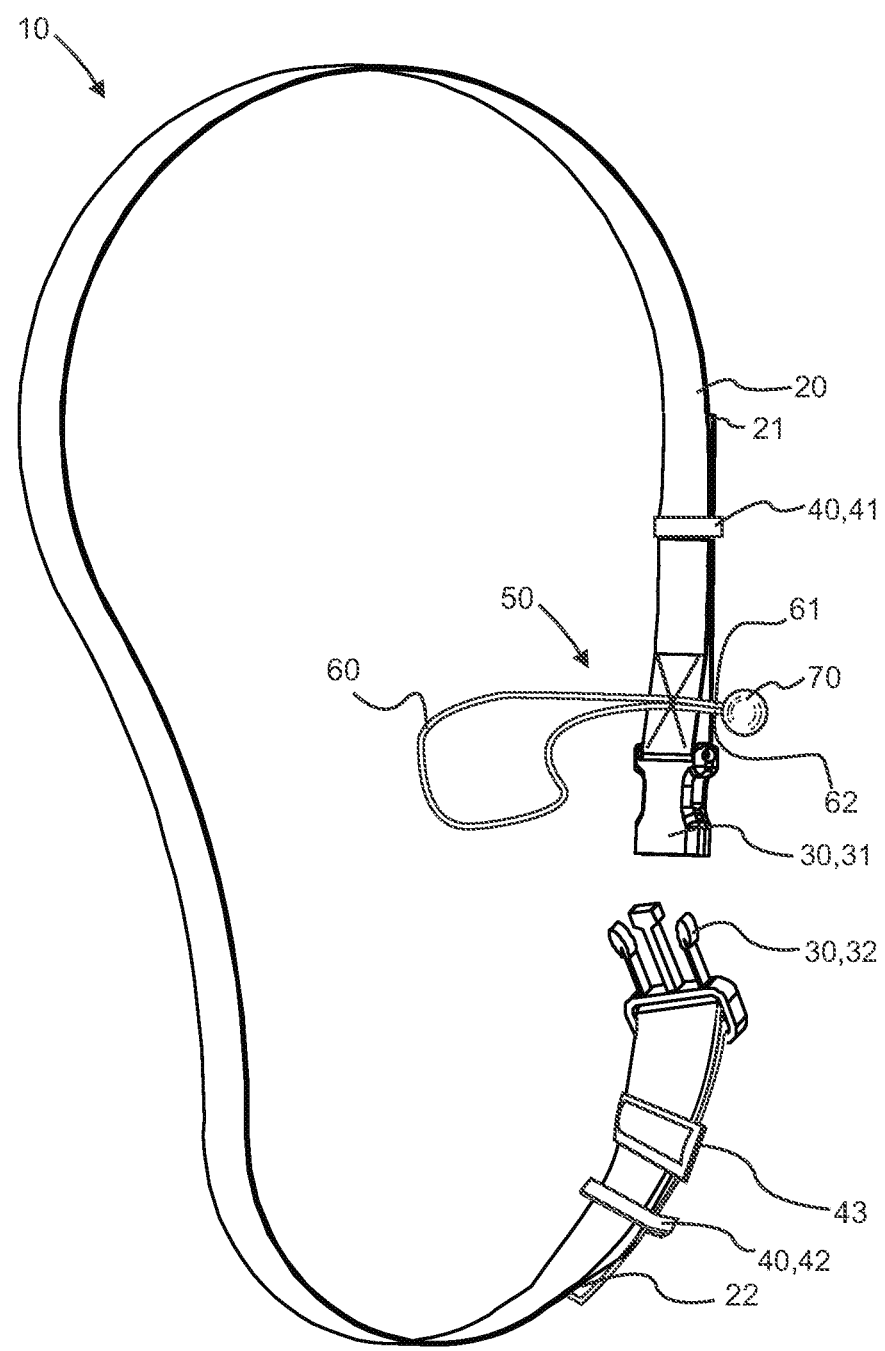
FIG. 1 is a perspective view of the leg restraint system according to select embodiments of the instant disclosure.
Figure 2:
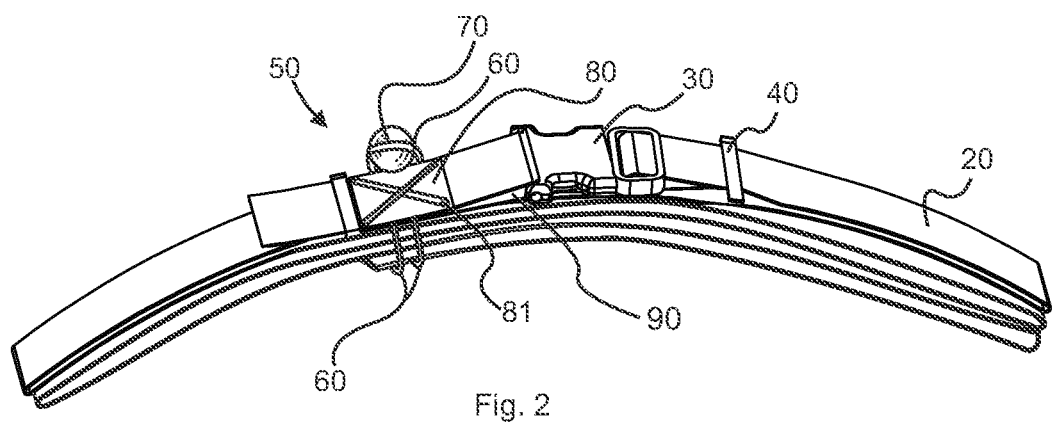
FIG. 2 is a perspective view of the leg restraint system of FIG. 1, shown folded for storage to the seating area.
Figure 3:
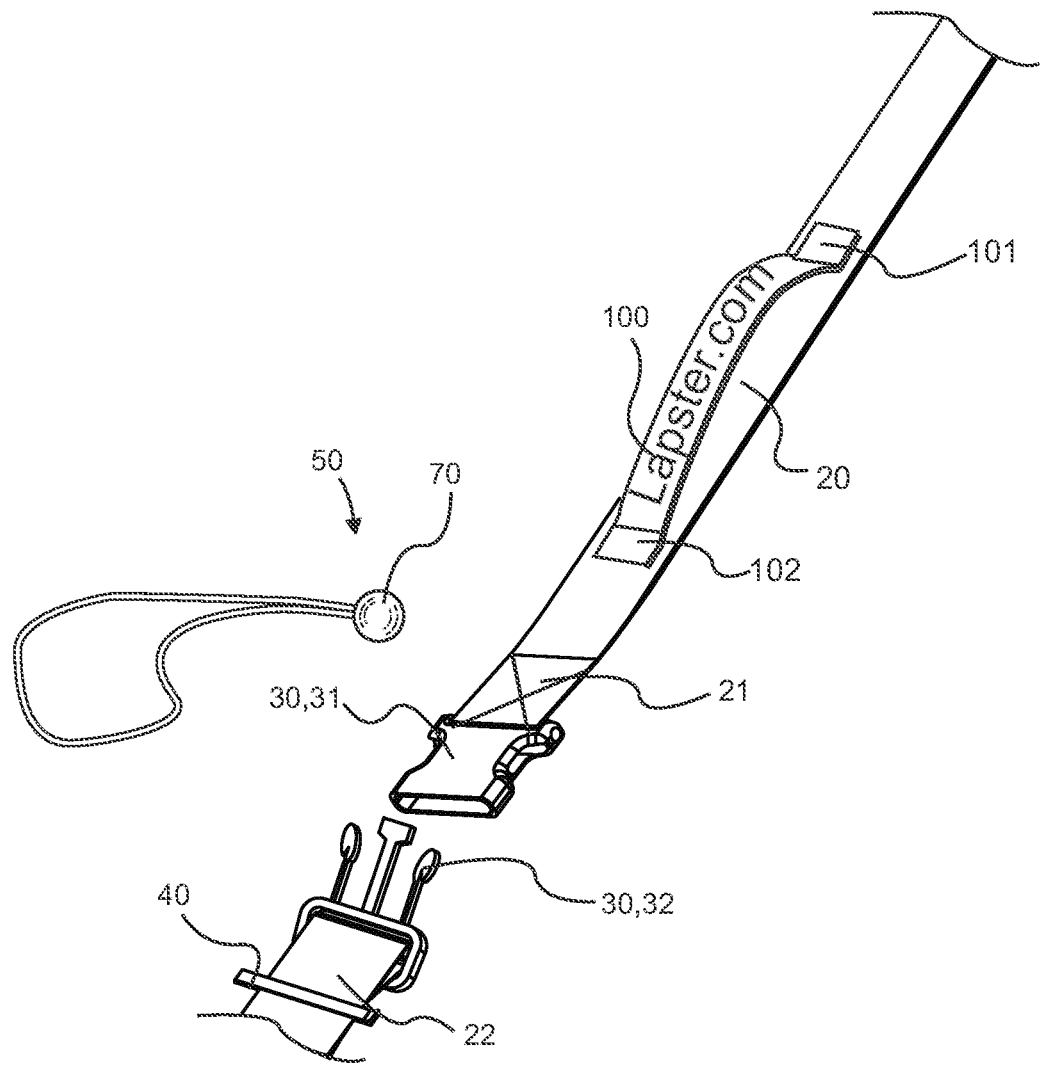
FIG. 3 is an exploded perspective view of the leg restraint system of FIG. 1, showing latch mechanism.

Referring now to FIGS. 1-3, by way of example, and not limitation, there is illustrated an example embodiment of leg restraint system 10 configured having an elongated band, such as strap 20. Strap 20 may include first strap end 21 and second strap end 22. Strap 20 may be constructed of any bendable and soft material such as nylon, polyester or other durable polymer or organic similar material, as these material offers a variety of widths and lengths; however, other suitable materials or the like, can be utilized, provided such material has sufficient strength, flexibility, softness to maintain the size, configuration and purpose of strap 20. Moreover, strap 20 may be configured to have a variety of widths and lengths while maintaining the purpose herein; however, preferably strap 20 may have a two inch width and a sixty inch length to accommodate most users U. It is contemplated herein that other widths and lengths may be utilized herein.

First strap end 21 and second strap end 22 may be connected or affixed or slidably affixed thereto a removable latch, such as quick release latchable buckle 30 having first latchable end, such as female buckle 31 and second latchable end, such as male buckle 32 configured to clasp, insert therein and be releasably latched one to the other. Moreover, female buckle 31 may be affixed or slidably affixed proximate first strap end 21 and male buckle 32 may be affixed or slidably affixed proximate second strap end 22 of strap 20. Clasped, clasping or latching female buckle 31 thereto male buckle 32 temporarily affixes first strap end 21 and second strap end 22. Furthermore, first strap end 21 may extend through or overlap female buckle 31 by a short length, like approximately two inches and sewn 81 back to itself to make fold 90 or alternatively patch 80 made of polyester or other similar material as strap 20 may be sewn 81 thereon first strap end to strengthen fold 90. Moreover, strap 20 may include a strap loop or handle, such as strap handle 100 having first strap handle end 101 and second strap handle end 102 attached thereto strap 20. Alternatively, first strap handle end 101 and second strap handle end 102 of strap handle 100 may fold back on itself where first strap handle end 101 and second strap handle end 102 are proximate one another and attach thereto strap 20 to form a loop. Preferably, strap handle 100 may be utilized to grip (gripped) or tug thereon first strap end 21 to tighten leg restraint system 10 around user U. Moreover, strap handle 100 may include indicia, like "LAPSTER" marked thereon strap handle 100 for advertising and marketing purposes.

First strap end 21 and second strap end 22 may each include keeper 40, configured to attach strap ends to strap 20, such as first keeper 41 may be utilized to gather, affix, or attach excess first strap end 21 thereto strap 20 and second keeper 42 may be utilized to gather, affix, or attach excess second strap end 22 thereto strap 20.

Second strap end 22 of strap 20 may include slide 43 positioned in a loop back of strap 20 around male buckle 32 preferably between male buckle 32 and second keeper 42 and utilized to adjust and hold second strap end 22 as well as adjust and hold the overall length of strap 20.

It is recognized herein that quick release buckle 30 and keeper 40 may be constructed of metal, steel, alloy, polymer, or plastic or more specifically high density polyethylene, polyethylene terephthalate (PETG), acrylonitrile butadiene styrene (ABS), polypropylene (PP), polyoxymethylene (POM), polyvinyl chloride (PVC) or similar high tensile or strengthened materials, as these material offers a variety of forms and shapes and provide strength and are non-metallic; however, other suitable materials or the like, can be utilized, provided such material has sufficient strength, able to maintain the latch function, configuration and integrity of buckle 30 and keeper 40. Moreover, buckle 30 and keeper 40 may be 3D printed, vacuum or injection molded, or extruded from the above material to form buckle 30 and keeper 40.

Leg restraint system 10 may include a stretchable binder, such as bungee binder 50. Bungee binder 50 may include elongated stretch cord 60. Stretch cord 60 may include first cord end 61 and second cord end 22. Stretch cord 60 may be constructed of any stretchable or elastic material such as nylon, polyester or other durable polymer or organic similar material having strands of spandex or other stretch material; however, other suitable materials or the like, can be utilized, provided such material has sufficient stretchability to stretch and maintain the length, configuration and purpose of stretch cord 60. Moreover, stretch cord 60 may be configured to have a variety of lengths while maintaining the purpose herein; however, preferably stretch cord 60 may have approximately a twelve inch length to accommodate extending around a folded or coiled strap 20 to secure or transport leg restraint system 10 when not in use. It is contemplated herein that other lengths may be utilized herein. Bungee binder 50 may include stopper, such as ball 70 to gather looped stretch cord 60, or more specifically to gather first cord end 61 and second cord end 22 to configure stretch cord 60 in a loop utilized to be stretched and loop over ball 70 to hold folded or coiled strap 20 in tight configuration to store or transport leg restraint system 10 when not in use (stored position). If rolling, strap 20 may be rolled from second strap end 22 to first strap end 21 where bungee binder 50 may be located and bungee binder 50 may be utilized to secure rolled strap 20 when not in use (stored position).

It is contemplated herein that bungee binder 50 may be affixed or releasably affixed thereto strap 20, buckle 30, or keeper 40. Preferably bungee binder 50 is affixed to strap 20 proximate first strap end 21 or second strap end 22. Moreover, bungee binder 50 may be positioned in, inserted therein, or fed through fold 90 of first strap end 21 or second strap end 22 where first strap end 21 or second strap end 22 connects thereto female buckle 31 and male buckle 32, respectively. Alternatively, bungee binder 50 may be affixed to strap 20 proximate first strap end 21 or second strap end 22 by a stitched fabric, such as patch 80 sewn 81 over stretch cord 60 with stretch cord 60 positioned between first strap end 21 or second strap end 22 and patch 80.

Figure 4:
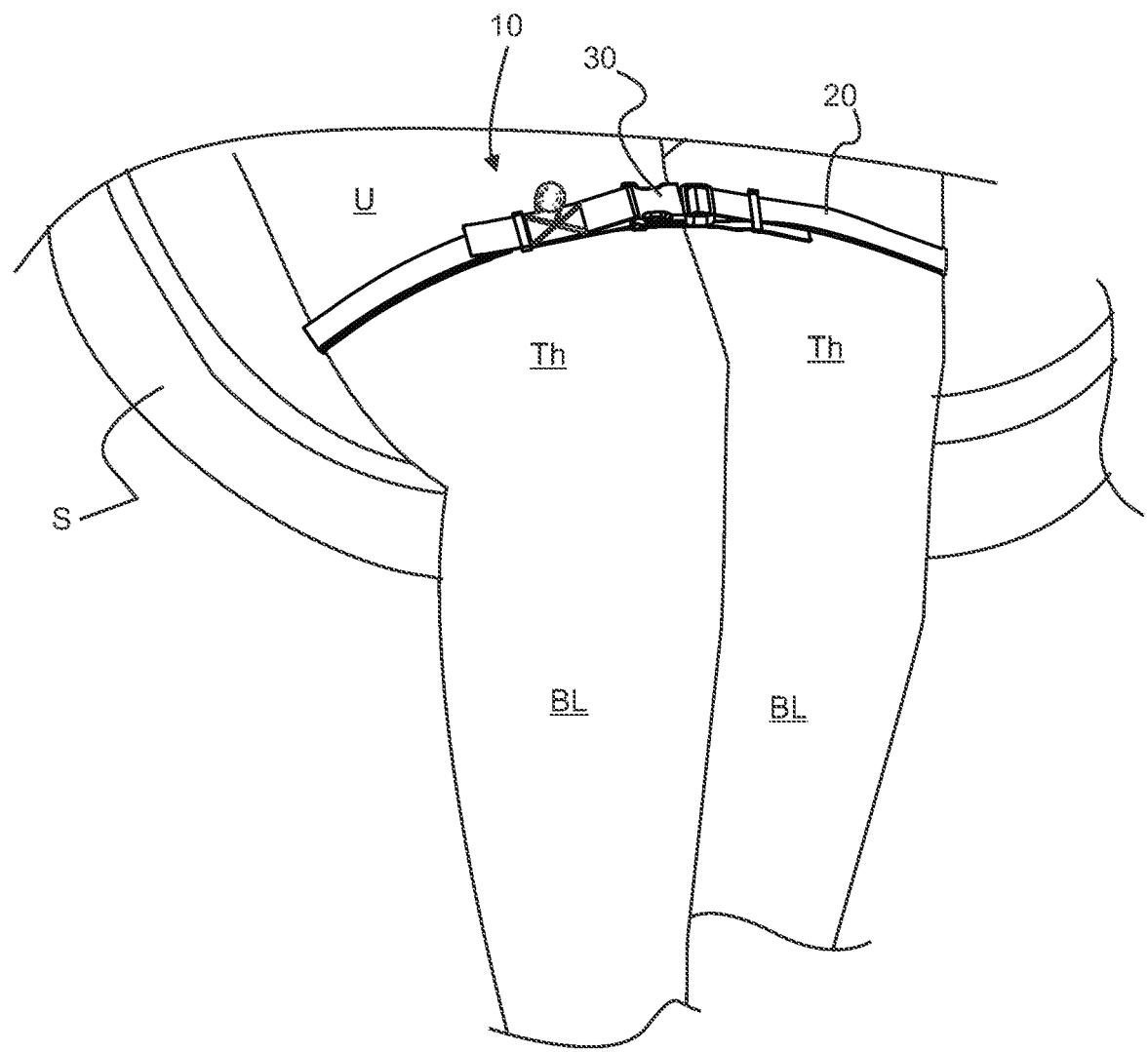
FIG. 4 is a perspective view of the leg restraint system of FIG. 1, shown in use by a seated traveler.

Referring now to FIG. 4, by way of example, and not limitation, there is illustrated an example embodiment of leg restraint system 10 in use. A traveler, such as user U may be seated with bent legs BL on a seat in for example an airplane, train, bus, sport and other entertainment seating, or other public or private seating arrangement. User U may utilize leg restraint system 10 by wrapping strap 20 around user's thighs Th or thighs Th of user U and latching buckle 30 to hold (grasp and maintain in position) a seated passengers bent legs in parallel and prevent their bent legs BL from spreading to a V-spread and encroaching on another adjacent traveler's AT designated leg space G, called "manspreading".

Figure 5A:
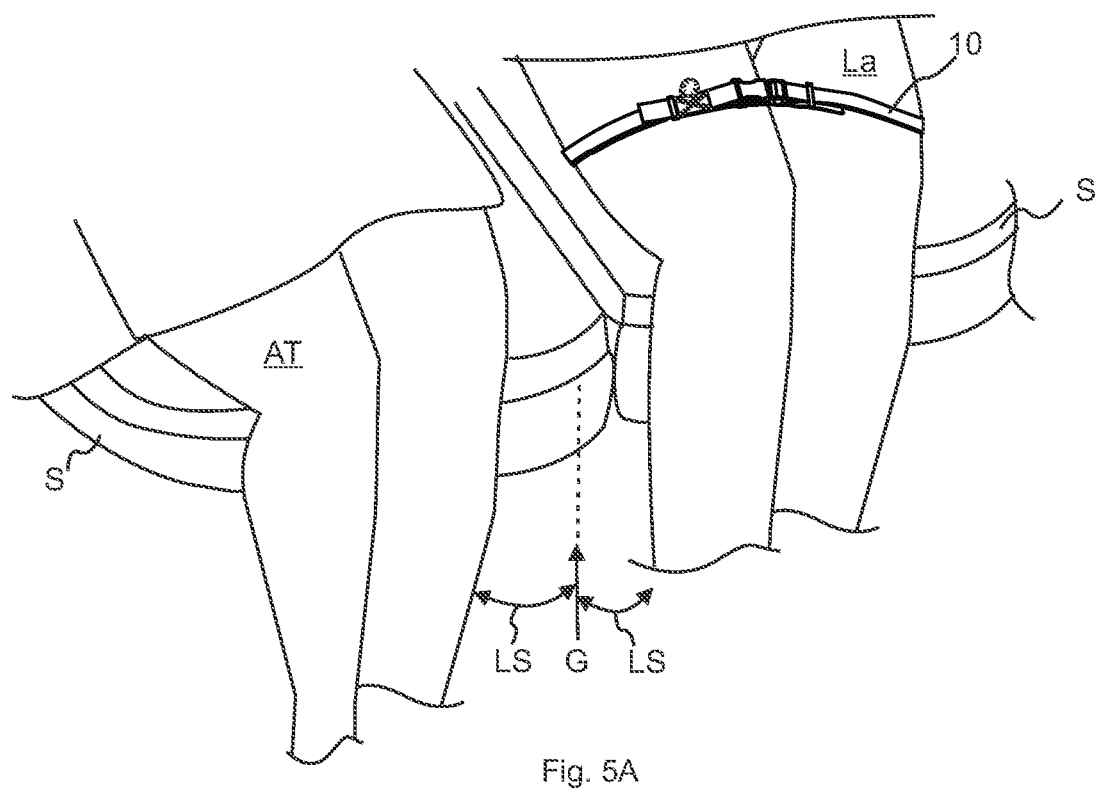
FIGS. 5A and 5B are a perspective view of the leg restraint system of FIG. 1, shown in use by one traveler seated next to another traveler.
Figure 5B:
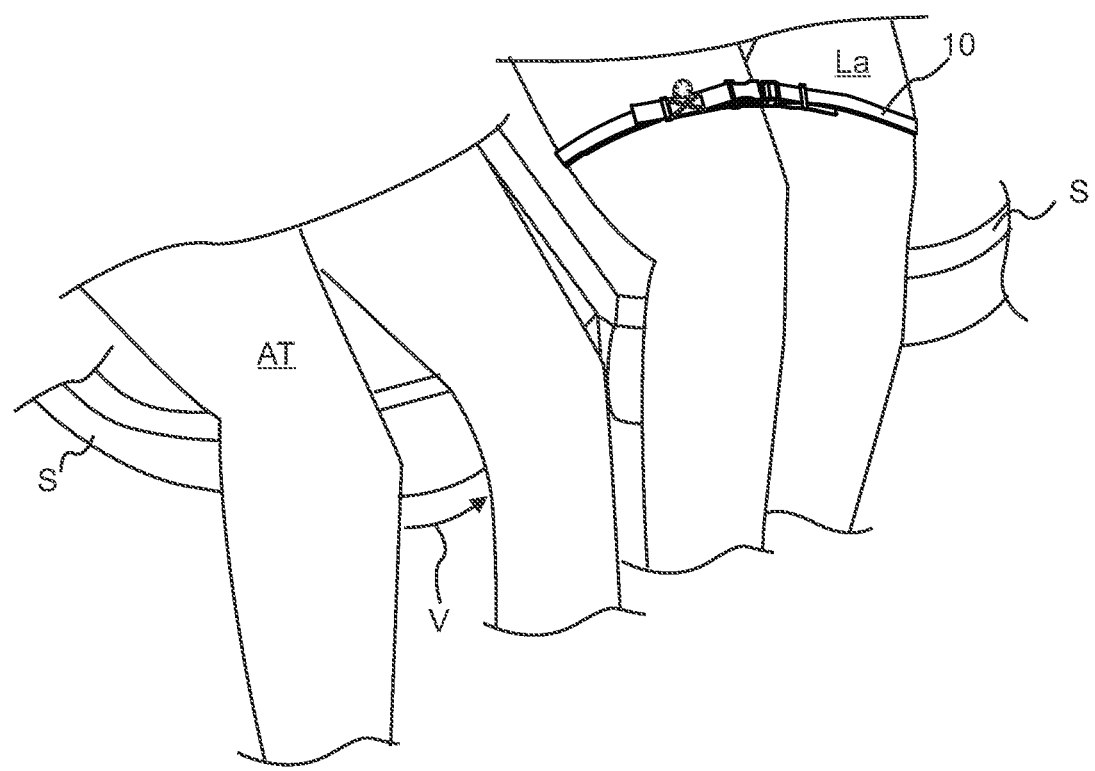
Figure 6:
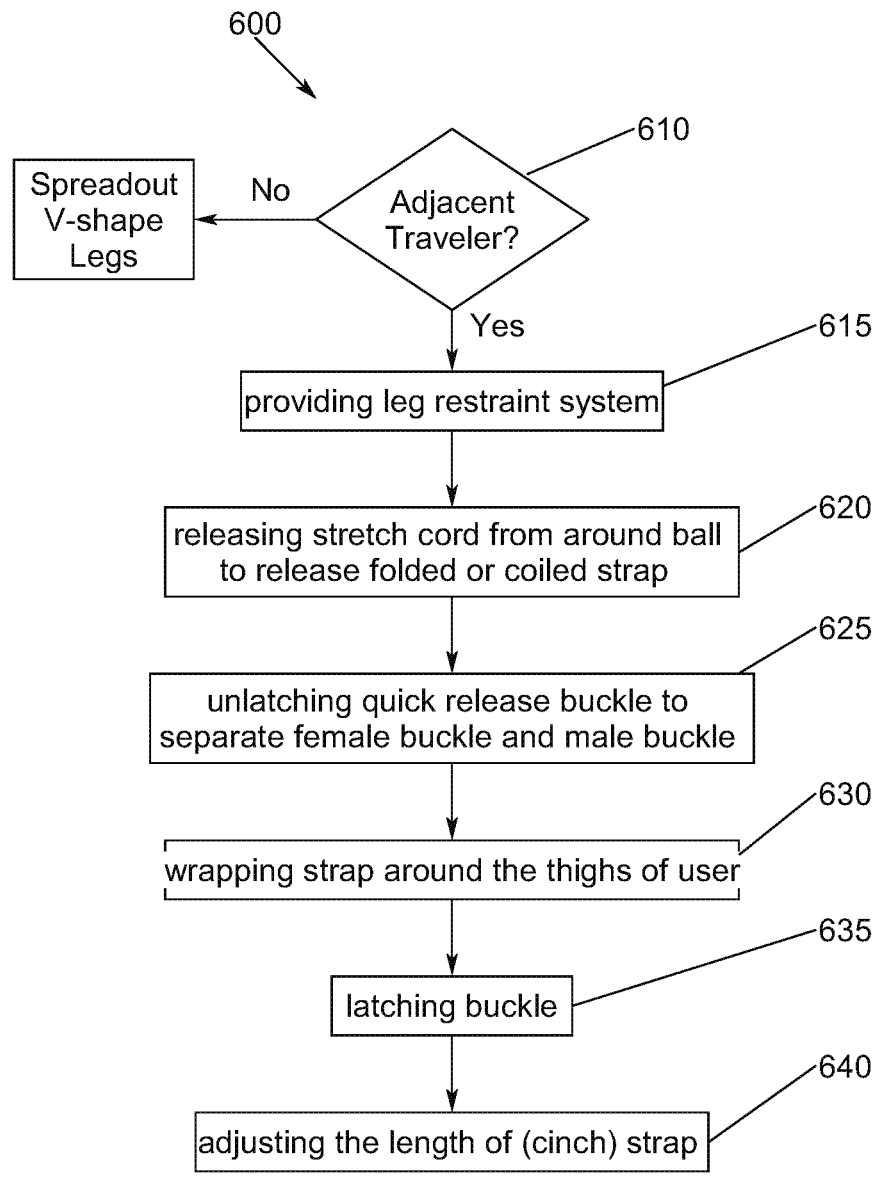
FIG. 6 is a flow diagram of a method of installation and use of leg restraint system to properly align one traveler's bent legs while seated to better maintain a person's thighs in their personal space.

Referring now to FIGS. 5A and 5B, by way of example, and not limitation, there is illustrated an example embodiment of leg restraint system 10 in use. A traveler, such as user U may be seated with bent legs BL on a seat in for example an airplane, train, buss, sport and other entertainment seating, or other public or private seating arrangement. User U may utilize leg restraint system 10 by wrapping strap 20 around their thighs Th and latching buckle 30 to hold a seated passengers bent legs BL in parallel and prevent their bent legs BL from spreading to a V-spread V and encroaching on another adjacent traveler's AT designated leg space LS, called "manspreading" shown in FIG. 5B as adjacent traveler's AT. In FIG. 5A, adjacent traveler AT is free to use their designated leg space without encroachment by user U. Moreover, utilize leg restraint system 10 may relieve inner thigh gripping tension during long or extended travel time while still maintain an adequate gap G for testicle spacing and cooling.

Referring now to FIGS. 1-5, and 6, there is illustrated a flow diagram 600 of a method for holding or securing user U thighs Th to hold a seated passengers bent legs BL in parallel and prevent their bent legs BL from spreading to a V-spread and encroaching on another adjacent traveler's AT designated leg space G, called "manspreading". In In block or step 610, determining whether adjacent traveler AT is present or likely to become present and seated next to user U. If no, may spread user U thighs Th to a V-spread. If yes, in block or step 615, providing leg restraint system 10 as set forth in any of the embodiments discussed herein, and/or shown in FIGS. 1-5. In block or step 620, releasing stretch cord 60 from around ball 70 of bungee binder 50 and unrolling, unravelling or unwinding strap 20. In block or step 625, unlatching quick release buckle 30 and remove female buckle 31 from male buckle 32 or if unbuckled, then the step completed. In block or step 630, wrapping strap 20 around the thighs Th of user U seated next to adjacent traveler AT. In block or step 635, latching buckle 30 by inserting male buckle 32 female buckle 31. In block or step 640, adjusting the length of (cinch) strap 20 and/or keeper 40 to prevent bent legs BL of user U from spreading to a V-spread and encroaching on another adjacent traveler's AT designated leg space G.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Moreover, the present disclosure has been described in detail, it should be understood that various changes, substitutions and alterations can be made thereto without departing from the spirit and scope of the disclosure as defined by the appended claims. Accordingly, the present disclosure is not limited to the specific embodiments illustrated herein but is limited only by the following claims.

The invention claimed is:
1. A leg restraint system to hold a person's thighs together while seated with bent legs, said system comprising:
   a strap having a first strap end and a second strap end;
   a buckle, said buckle having a first latchable end and a second latchable end, wherein said first latchable end is affixed to said first strap end and said second latchable end affixed to said second strap end, wherein said first strap end extends through said first latchable end and is folded on itself to form a fold and sewn to affix said first latchable end thereto said first strap end;

one or more keepers configured to gather said first strap end and said second strap end;
a slide affixed to said second strap end to adjust a length of said strap, said slide positioned between said second latchable end and said one or more keepers;
a bungee binder, said bungee binder configured to hold said strap in a stored position, said bungee binder further comprising a ball and a stretch cord configured as a loop extending therefrom said ball, wherein said stretch cord is affixed at said first strap end within the fold.

2. The system of claim 1, wherein said first strap end is configured to have a strap handle.

3. The system of claim 2, wherein said strap handle is configured to be gripped to cinch said strap therearound the person's thighs.

4. The system of claim 1, wherein said strap is configured to extend around the person's thighs and said first latchable end and said second latchable end are configured to be clasped together to hold the person's thighs together.

5. A method of holding a user's thighs together while seated with bent legs, said method comprising the steps of:
    determining whether an adjacent traveler is present next to the user;
    providing a leg restraint system with a strap having a first strap end and a second strap end, a buckle, said buckle having a first latchable end and a second latchable end, wherein said first latchable end is affixed to said first strap end and said second latchable end affixed to said second strap end, one or more keepers configured to gather said first strap end and said second strap end, a slide affixed to said second strap end to adjust a length of said strap, said slide positioned between said second latchable end and said one or more keepers, and a bungee binder having a ball and a stretch cord configured as a loop extending therefrom said ball, said bungee binder configured to hold said strap in a stored position;
    releasing said stretch cord from around said ball to unravel said strap;
    wrapping said strap around the thighs of user; and
    latching said buckle by inserting said first latchable end into said second latchable end.

6. The method of claim 5, adjusting said strap therein said slide to prevent the bent legs of the user from spreading to a V-spread.

* * * * *